(12) United States Patent
Akiyama

(10) Patent No.: US 6,174,419 B1
(45) Date of Patent: Jan. 16, 2001

(54) ELECTROLYTIC WATER PRODUCING APPARATUS

(75) Inventor: Osamu Akiyama, Tokyo (JP)

(73) Assignees: Shimadzu Corporation, Kyoto; Water Research Institute, Tsukuba, both of (JP)

(*) Notice: Under 35 U.S.C. 154(b), the term of this patent shall be extended for 0 days.

(21) Appl. No.: 09/309,897

(22) Filed: May 11, 1999

(30) Foreign Application Priority Data

May 28, 1998 (JP) .................................................. 10-147170
Apr. 9, 1999 (JP) .................................................. 11-103405

(51) Int. Cl.[7] .............................. B23H 3/02; C25B 9/00; C25C 3/16; C25D 17/00; C25F 7/00
(52) U.S. Cl. .................................... 204/228.6; 204/229.4; 204/229.6; 204/229.5
(58) Field of Search .............................. 204/228.1, 228.6, 204/229.4, 229.5, 229.6; 205/744

(56) References Cited

U.S. PATENT DOCUMENTS 5,304,289 * 4/1994 Hayakawa .......................... 205/701
5,858,201 * 1/1999 Otsuka et al. ...................... 205/701

* cited by examiner

Primary Examiner—Kathryn Gorgos
Assistant Examiner—Wesley A. Nicolas
(74) Attorney, Agent, or Firm—Kanesaka & Takeuchi

(57) ABSTRACT

In an electrolytic water producing apparatus, an anode and a cathode in an electrolytic cell are periodically switched to reduce degradation thereof. The concentration of hypochlorous acid formed in the strong acidic liquid is measured through a concentration sensor, and a concentration variation pattern varying in a sawteeth pattern according to the switching of the anode and cathode is taken into a control device. A control pattern inversely corresponding to the sawteeth pattern is calculated by the controlling device. Electrolytic current or voltage to be supplied to the electrodes may be controlled according to the control pattern, or supply quantities of raw water or a chloride solution may be controlled by a flow rate controlling valve and a metering pump. Thus, although the polarities of the electrodes are switched, the strong acidic liquid containing hypochlorous acid with a constant concentration can be obtained.

8 Claims, 4 Drawing Sheets

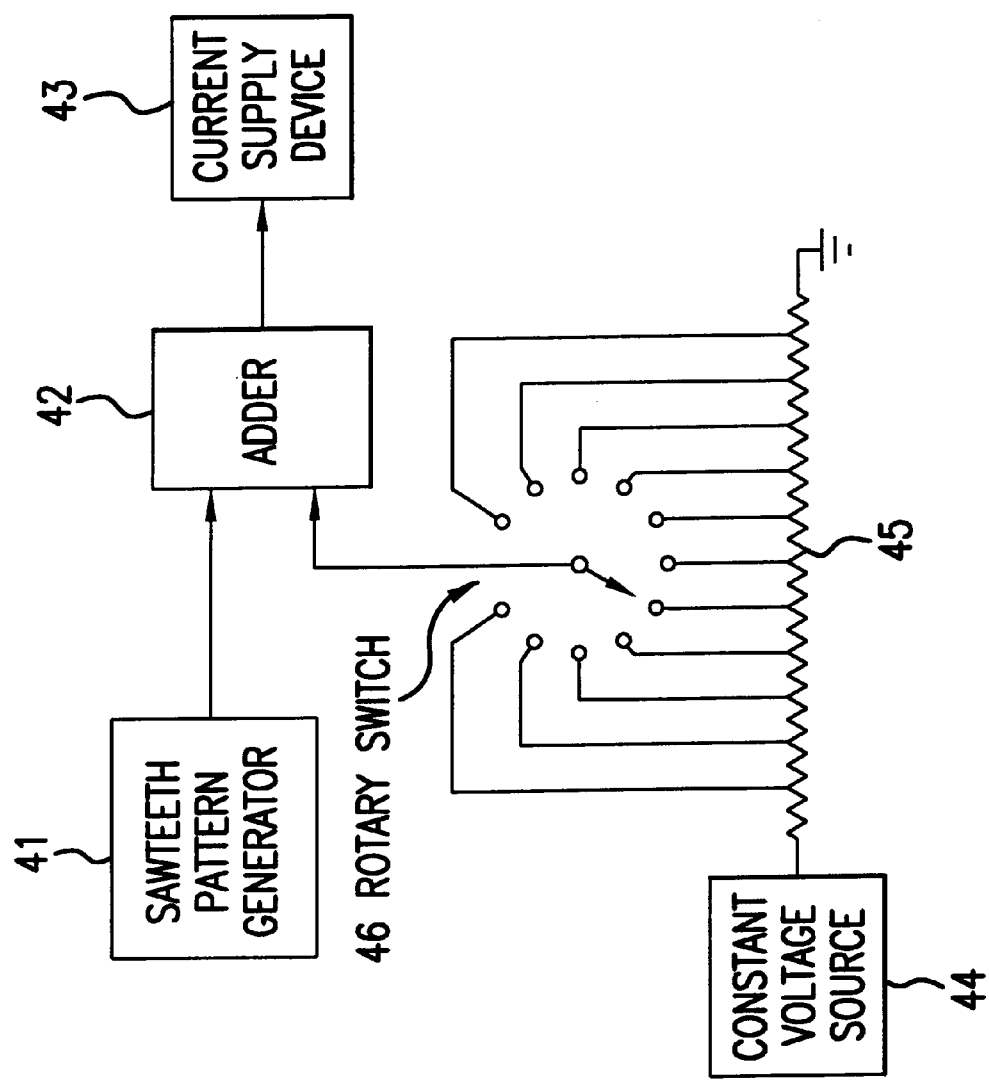

ELECTROLYTIC WATER PRODUCING APPARATUS

BACKGROUND OF THE INVENTION AND RELATED ART STATEMENT

The present invention relates to an electrolytic water producing apparatus to be used in a medical field, food industry, agriculture or the like, in particular to an electrolytic water producing apparatus which has been improved in keeping a concentration of hypochlorous acid contained in a produced strong acidic liquid constant.

An electrolytic water producing apparatus produces a strong acidic liquid on an anode side and a strong alkaline liquid on a cathode side, respectively, by electrolyzing a chlorine-containing-liquid. In case water contains chlorine, the strong acidic liquid produced on the anode side contains hypochlorous acid having a sterilization ability. Especially, in case a mixture of a solution of chloride, such as sodium chloride or potassium chloride, and water is subjected to electrolysis, a strong acidic liquid produced on the anode side contains several tens of ppm of hypochlorous acid, and shows a low pH of 2.5 to 3.0 and high ORP (oxidation reduction potential) of about +1100 mV. The strong acidic liquid has been known to have a high sterilization effect.

Therefore, the thus produced strong acidic liquid has been used for disinfecting hands or the like in a hospital or sterilizing MRSA causing infection in the hospital in a medical field; for disinfecting or sterilizing kitchen instruments in a food industry; for sterilizing fishes in a marine product processing industry; and for sterilizing O-157. Also, in an agricultural field, the strong acidic liquid obtained by subjecting water containing potassium chloride to electrolysis has been used for disinfection or killing pathogen for melons, vegetables, pears, flowers or the like in a house cultivation, or for sterilizing unhulled rices to thereby reduce an amount of pesticide to be used in considering the environments.

However, in a conventional electrolytic water producing apparatus, there has been a defect such that it is not confirmed whether a strong acidic liquid having a sterilizing effect is produced or not, i.e. hypochlorous acid in the strong acidic liquid has a predetermined concentration. Actually, some of the electrolytic water producing apparatuses which have been sold on the market do not control the concentration of hypochlorous acid. Even if the brochures for the electrolytic water producing apparatuses are referred to, values for covering a very wide range, such as 20 to 50 ppm, have only been cited.

In view of the above, the present invention has been made, and an object of the invention is to provide an electrolytic water producing apparatus, which has been improved in producing an acidic liquid wherein the concentration of hypochlorous acid contained therein is always kept constant.

Another object of the invention is to provide an electrolytic water producing apparatus as stated above, which can be easily maintained and controlled so that a user can use without anxiety.

Further objects and advantages of the invention will be apparent from the following description of the invention.

SUMMARY OF THE INVENTION

An electrolytic water producing apparatus of the invention includes a device for supplying raw water; a device for supplying a chloride solution; a device for mixing the supplied raw water and chloride solution; an electrolyzing device for producing a strong acidic liquid on an anode side and a strong alkaline liquid on a cathode side, respectively, by electrolyzing the mixed liquid; a measuring device for measuring a concentration of hypochlorous acid contained in the strong acidic liquid produced on the anode side; and a controlling device for periodically switching polarities of electrodes in the electrolyzing device and, at the same time, controlling electrolytic conditions with an inverse sawteeth pattern inversely corresponding to a sawteeth pattern of the measured concentrations of the hypochlorous acid according to the polarity changes.

The above controlling device can control any one or a plurality of a supply quantity of the raw water; a supply quantity of the chloride solution; and voltage or current to be applied to the anode and cathode in the electrolyzing device.

The inverse sawteeth control pattern may be set in the controlling device beforehand. The inverse sawteeth control pattern may be formed of lines similar to straight lines.

The inverse sawteeth control pattern may be set in the controlling device beforehand by calculating through the controlling device using concentrations of hypochlorous acid in the strong acidic liquid measured by the measuring device under the condition where control of the electrolytic conditions is temporarily stopped at any time.

The concentration of hypochlorous acid in the strong acidic liquid obtained at a time of controlling the electrolytic conditions is measured by the measuring device, and the controlling device may shift the controlling pattern as a whole according to the measured value. The shift quantity may be manually switched.

In the measuring device, a light quantity absorbed by hypochlorous acid ions in a mixture of the strong acidic liquid produced on the anode side and the strong alkaline liquid produced on the cathode side may be measured.

The measuring device may employ an electrochemical sensor according to a constant potential coulometry method or a constant current coulometry method.

Polarities of the electrodes in the electrolyzing device are periodically switched for protection of the electrodes. Therefore, the concentration of hypochlorous acid in the strong acidic liquid is high right after the polarity is switched and thereafter is gradually lowered to form a sawtooth pattern. The sawtooth pattern is repeated whenever the polarity is switched, to form sawteeth pattern. Therefore, an inverse sawteeth control pattern inversely corresponding to the sawteeth pattern is obtained, and when the electrolytic conditions are controlled based on the inverse sawteeth control pattern according to switching of the polarities, the concentration of hypochlorous acid in the strong acidic liquid can be kept constant.

If the control pattern is obtained by measuring the concentration of hypochlorous acid in the strong acidic liquid at a time of shipment of the electrolytic water producing apparatus from a factory or installation thereof to a user's site and the obtained control pattern is set in the control device beforehand, the user need not make any setting operation and can produce the strong acidic liquid containing hypochlorous acid having a predetermined concentration without troublesome operation.

In case the control pattern is obtained by using the measuring device in a state wherein control of the electrolytic condition is temporarily stopped at any desired time and calculating the control pattern using the measured results obtained by the controlling device and the obtained control pattern is set in the controlling device, variations of the concentration of hypochlorous acid in the strong acidic liquid caused by environmental changes, deteriorated electrodes' surfaces due to use for a long period of time or the like, can be offset. Therefore, the electrolytic water producing apparatus of the invention can produce the strong acidic liquid containing hypochlorous acid with a constant concentration.

BRIEF DESCRIPTION OF THE DRAWINGS

FIG. 6 is a block diagram showing an example of a circuit for controlling a shift quantity.

DETAILED DESCRIPTION OF PREFERRED EMBODIMENTS

With reference to the accompanying drawings, embodiments of the present invention are explained in detail.

Figure 1:
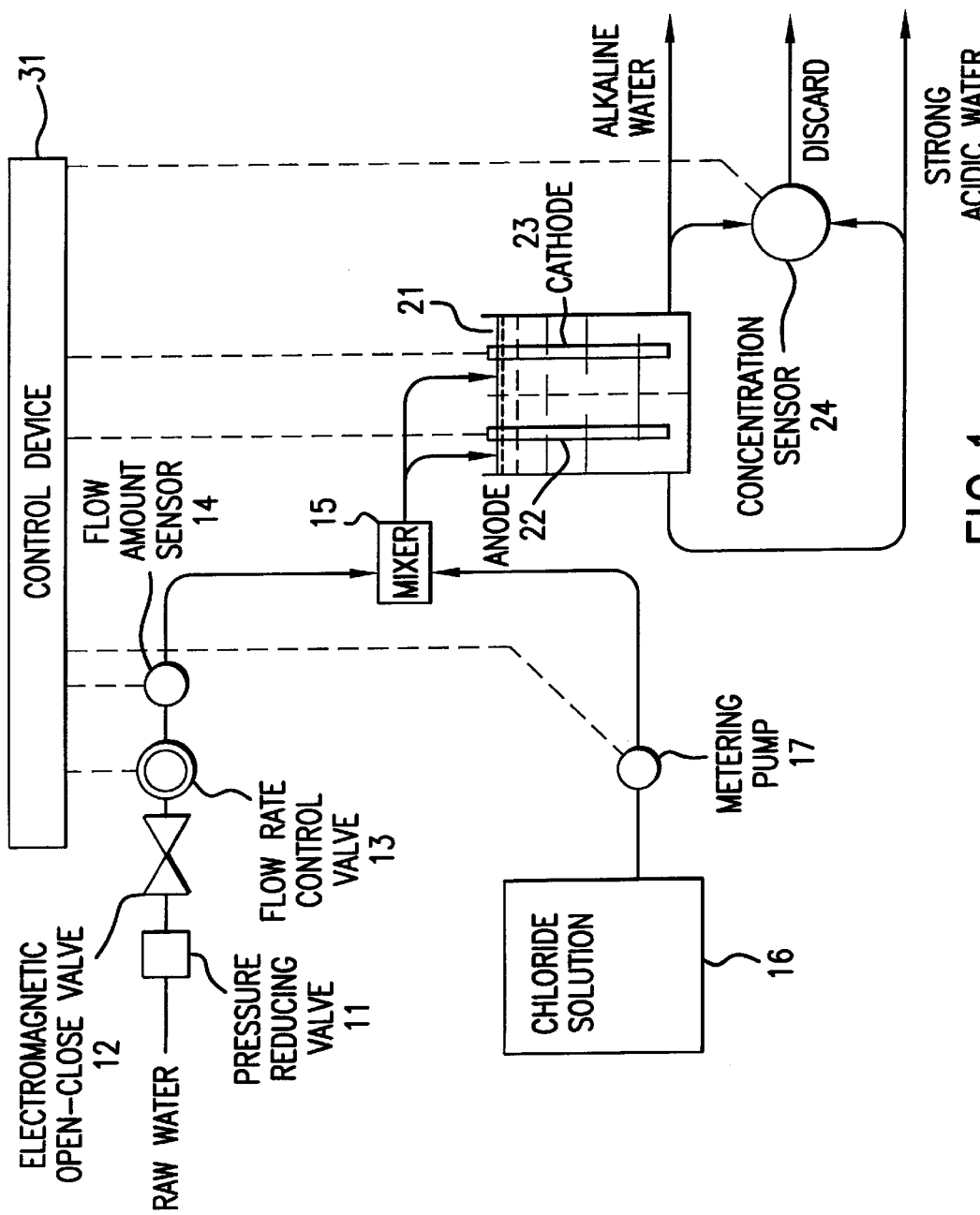
FIG. 1 is a block diagram of an electrolytic water producing apparatus of an embodiment according to the invention.

In FIG. 1, raw water, such as tap water, is transferred to a mixer 15 through a pressure-reducing valve 11, electromagnetic open-closing valve 12, flow rate control valve 13 and flow amount sensor 14. On the other hand, a high concentrated chloride solution 16, such as high concentration aqueous solution with chloride, for example, NaCl or KCl, is supplied to the mixer 15 through a metering pump 17. Raw water and chloride solution 16 are mixed in the mixer 15 to obtain a chloride concentration of about 0.1%. The thus obtained diluted liquid is supplied to an anode 22 side and a cathode 23 side of an electrolytic cell or container 21 to be subjected to electrolysis therein, so that a strong acidic liquid is produced on the anode 22 side and a strong alkaline liquid is produced on the cathode 23 side, respectively. These liquids are supplied for using.

A part of the strong acidic liquid and a part of the strong alkaline liquid are sent to a concentration sensor 24 to determine a concentration of hypochlorous acid. The concentration sensor 24 determines the concentration of hypochlorous acid in such manner that the strong acidic liquid is mixed with the strong alkaline liquid to raise a pH value of the mixture, so that hypochlorous acid contained in the strong acidic liquid is dissociated to hypochlorous acid ions having an absorption characteristic in the vicinity of a wavelength of 292 nm, and an absorption degree thereof is measured to determine the concentration of hypochlorous acid. Incidentally, in case an electrochemical sensor according to a coulometric analyzing method is used, since the concentration of hypochlorous acid contained in the strong acidic liquid can be directly determined, it is not required to mix the strong alkaline liquid therewith, and only the strong acidic liquid is introduced thereto.

A controlling device 31 periodically switches the anode 22 and the cathode 23 to protect them, i.e. inverses polarities of voltages to be applied to the respective electrodes. Also, the controlling device 31 controls electrolytic conditions according to the concentration of hypochlorous acid in the strong acidic liquid determined by the concentration sensor 24 to thereby keep the concentration of hypochlorous acid in the produced strong acidic liquid approximately constant. Electrolytic conditions to be controlled include an electrolytic voltage, electrolytic current, supply quantity of the chloride solution 16 and supply quantity of raw water, at least one of which is changed. More specifically, the controlling device 31 switches the polarities of the electrodes 22 and 23; controls the flow rate control valve 13 by receiving a flow rate signal from the flow rate sensor 14 to thereby supply a predetermined flow rate of raw water to the mixer 15; and controls a supply quantity of the chloride solution 16 to be fed to the mixer 15 by controlling the metering pump 17.

Figure 2:
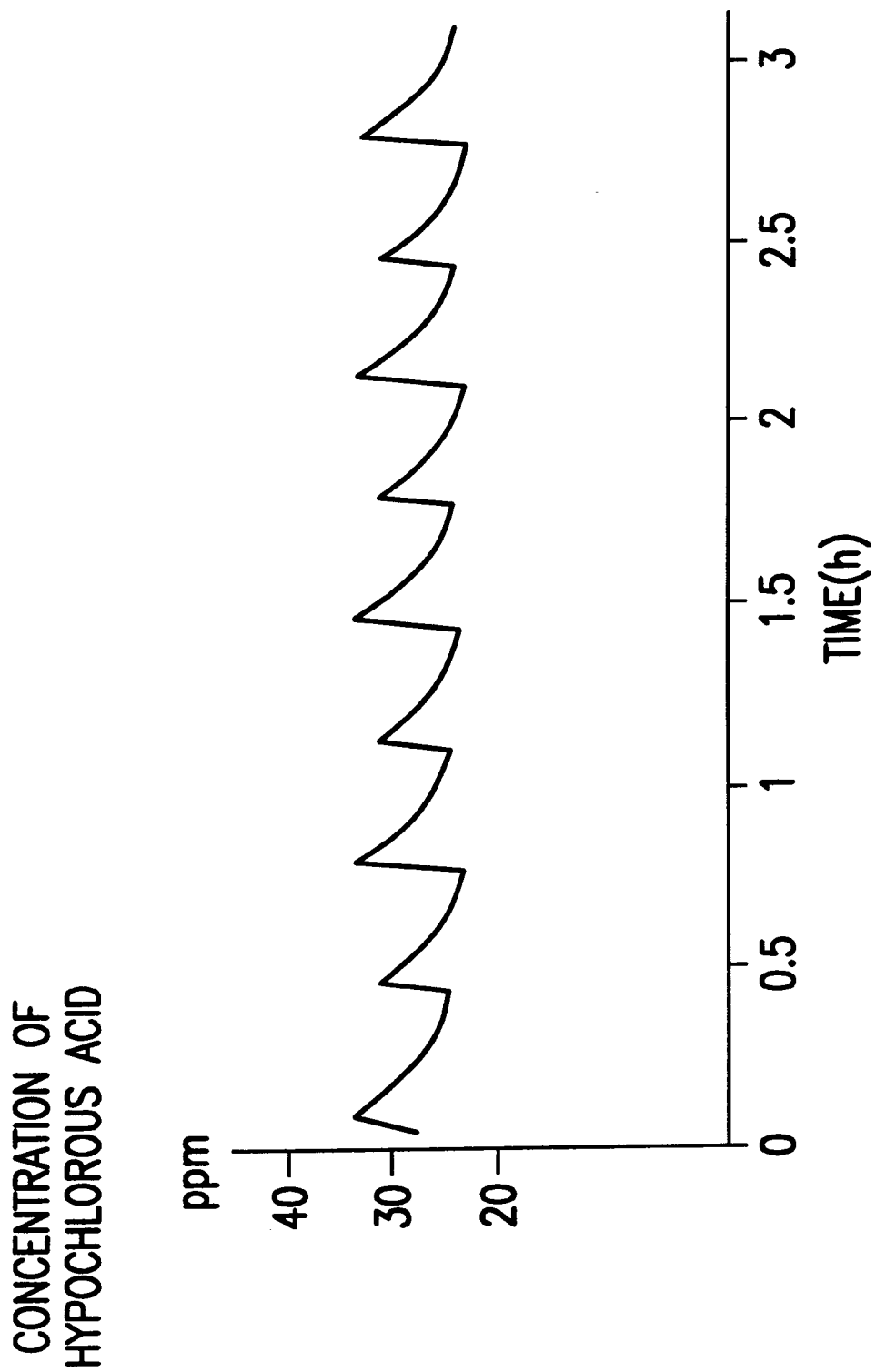
FIG. 2 is a time chart showing a timewise variation of a concentration of hypochlorous acid in a strong acidic liquid measured by the inventor.

In case the concentration of hypochlorous acid in the strong acidic liquid is not controlled to be constant and is measured, the concentration of hypochlorous acid contained in the strong acidic liquid repeats a sawteeth pattern as shown in FIG. 2. More specifically, the concentration of hypochlorous acid is temporarily increased right after an initialization and switching of polarities, and thereafter, it is generally decreased indexwise. The ratio of the maximum value and the minimum value of the sawteeth pattern is normally about ⅔, but it may be less than ½ as the case may be. Moreover, daily variation of the average concentration becomes large. Also, naturally, the concentration may be affected by seasonal water temperature variation and regional water quality variation. The sawteeth pattern in FIG. 2 is slightly different at the odd numbers and the even numbers in switching of polarities, which is considered to be caused by a little difference between the two electrodes.

Therefore, an example where only electrolytic current out of the four electrolytic conditions is controlled according to the measured value of the concentration of hypochlorous acid, is explained hereunder. First, the concentration of hypochlorous acid in the strong acidic liquid is measured at a time of a test run when an electrolytic water producing apparatus is shipped from a factory or at a time of installation of the apparatus to a user's site to obtain a sawteeth pattern concentration curve. Then, an inverse sawteeth pattern inversely corresponding to the sawteeth pattern is obtained from the sawteeth pattern through a calculation process and memorized in the controlling device 31. In case the user actually uses the apparatus, the concentration determination through the concentration sensor 24 need not be carried out, and the electrolytic current is controlled based on the inverse sawteeth pattern only according to switching of the polarities. More specifically, the current level is lowered right after the polarities are switched, and thereafter the current is gradually increased. This pattern is repeated whenever the polarities are switched.

Figure 3:
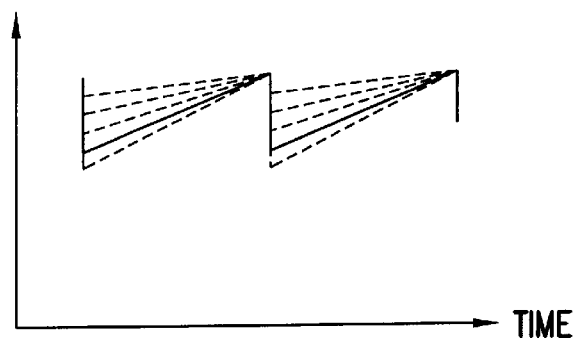
FIG. 3 is a time chart showing an example of a wave shape of an electrolytic current controlled to an inverse sawteeth pattern.
Figure 4:
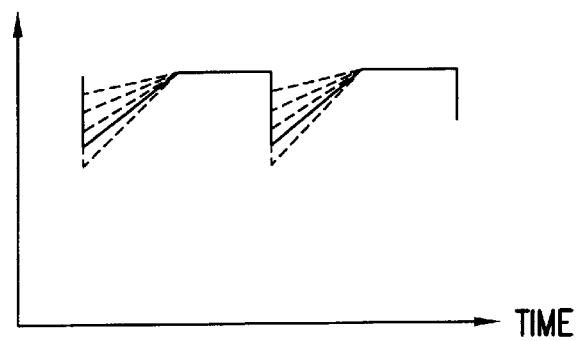
FIG. 4 is a time chart showing another example of a wave shape of an electrolytic current controlled to an inverse sawteeth pattern.
Figure 5:
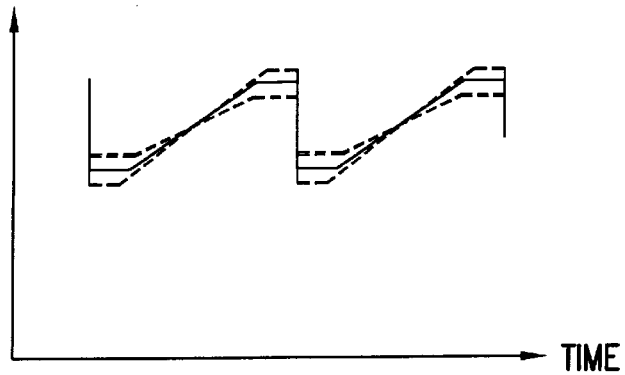
FIG. 5 is a time chart showing still another example of a wave shape of an electrolytic current controlled to an inverse sawteeth pattern.

As the inverse sawteeth current pattern, patterns with straight lines as shown in FIGS. 3, 4 and 5 can be used. Even the inverse sawteeth patterns with such straight lines are sufficient in actual use. Incidentally, the patterns shown in FIGS. 4 and 5 are graphs formed of linear lines. In addition to these, although not shown, an inverse sawteeth pattern of any curve according to an exponential function, spline function or the like may also be used.

Also, on the user's side, after the concentration control is stopped, the concentration of hypochlorous acid in the strong acidic liquid may be measured at any time through the concentration sensor 24 to thereby obtain the inverse sawteeth pattern. In this case, in order to obtain the optimum electrolytic conditions, the inverse sawteeth pattern is calculated and memorized by using plural values of the concentrations measured by the concentration sensor 24 and according to an operational formula memorized in the controlling device 31 beforehand. Or, the inverse sawteeth pattern memorized beforehand as mentioned above may be modified. Thereafter, the electrolytic current is controlled according to switching of the polarities based on the inverse sawteeth pattern thus obtained. In this case, the electrolytic current may be controlled according to variation of the concentration of hypochlorous acid in the strong acidic liquid caused by degeneration of surfaces of both electrodes due to long-range use, which may be made under the circumstance of the user, at any time, for example, when the apparatus is started up daily, in order to obtain the inverse sawteeth pattern to keep the concentration of hypochlorous acid in the strong acidic liquid constant.

Further, in case the variation is gentle in the lapse of time, the inverse sawteeth pattern may be calculated once in a certain period, for example two weeks, based on the above obtained actual values and memorized, and the electrolytic current may be controlled by using the pattern until the next renewal comes.

Although a strong acidic liquid having an approximately constant concentration of hypochlorous acid can be obtained as mentioned above by controlling the concentration based on the memorized inverse sawteeth pattern, the value itself of the approximately constant concentration may be deviated from the actual value. The deviation is caused by variations of seasonal water temperature and water quality of raw water, or decrease in electrolytic efficiency due to change with passage of time of the electrodes. To cope with the situations, the concentration of hypochlorous acid in the strong acidic liquid is measured through the concentration sensor 24 at a suitable timing, and in case it is found out that there is a significant difference between the approximately constant concentration value and the concentration value separately set in the controlling device 31, the above mentioned inverse sawteeth pattern itself is shifted as a whole. More specifically, in case the concentration is generally higher than the set value, the current value showing the inverse sawteeth pattern is wholly lowered, or conversely, in case the concentration is generally lower than the set value, the current value is wholly raised.

In order to adjust the shift of the whole pattern as mentioned above, for example, a structure as shown in FIG. 6 is considered. In the structure, a voltage of an inverse sawteeth pattern is generated from a sawteeth pattern generator 41, and a DC offset voltage is added thereto from an adder 42, which are applied to a current supply device 43 as a controlling voltage. The current supply device 43 supplies a current corresponding to the inputted controlling voltage between the anode 22 and cathode 23. The offset voltage to be added can be varied by dividing a stable voltage from a constant voltage source 44 into different voltages by a voltage dividing resistant unit 45 and changing taps of the unit 45 by a rotary switch 46.

More specifically, in the example shown in FIG. 6, when it is found that the whole current values of the inverse sawteeth pattern are to be shifted due to the seasonal variation as described above, the rotary switch 46 is manually operated to vary the offset voltage to be added by, for example, ±5 steps wherein one step is about 5 to 6%. When an electrolytic solution is produced by controlling the current of the inverse sawteeth pattern with the former offset value, the concentration of hypochlorous acid in the strong acidic liquid is measured by the concentration sensor 24 for a period of about 2 to 6 times of a polarity switching cycle to thereby obtain an average value thereof. Then, it is determined how much the average value is deviated from the set value to obtain an offset value to be changed and to determine a shift quantity, and the rotary switch 46 is operated.

Of course, it is also possible to automatically control the shift quantity instead of the above mentioned manual operation. In that case, the rotary switch 46 is replaced by an electronic control switching device, and a shift quantity is calculated from the above measured average concentration value through CPU to automatically switch the electronic control switching device according thereto.

Incidentally, since the patterns in the odd number and the even number are different as described above, it is necessary to carry out the concentration measurement for obtaining a control pattern of the inverse sawteeth shape more than two cycles of the polarity switching. It is also desirable to control two cycles for the control pattern. In other words, different inverse sawteeth control patterns are employed for the odd number and even number. However, since such strict control is not practical in view of a cost, a control pattern for one cycle may be determined by using an intermediate value, i.e. average value, of data obtained by measuring more than two cycles.

Further, in the above example, the electrolytic current is controlled. However, there are relationships such that in case an electrolytic voltage is increased, the concentration of hypochlorous acid in the strong acidic liquid is increased; in case a supply quantity of raw water, such as tap water, is increased, the concentration of hypochlorous acid in the strong acidic liquid is lowered; and in case a supply quantity of the chloride solution, such as NaCl, is increased, the concentration of hypochlorous acid in the strong acidic liquid is increased. Therefore, from these relationships, it is possible to control any one or a combination of more than one of the electrolytic current, electrolytic voltage, supply quantity of raw water and supply quantity of chloride solution.

As described hereinabove, according to an electrolytic water producing apparatus of the invention, electrodes can be protected by periodically switching polarities of the electrodes in an electrolytic cell or container, and at the same time, a concentration of hypochlorous acid in a strong acidic liquid varying with a sawteeth pattern according to the switching of the polarities can be always kept constant by controlling electrolytic conditions with an inverse sawteeth control pattern, so that an acidic liquid always contains hypochlorous acid at a constant concentration. Therefore, in various using methods, the electrolytic water producing apparatus of the invention can be easily maintained and controlled, so that the user can use it is without anxiety.

While the invention has been explained with reference to the specific embodiments of the invention, the explanation is illustrative and the invention is limited only by the appended claims.

What is claimed is:

1. An electrolytic water producing apparatus comprising:
   a raw water supply device;
   a chloride solution supply device;
   a mixer connected to the raw water supply device and the chloride solution supply device for mixing raw water and chloride solution supplied from the respective devices;
   an electrolyzing device adapted to provide a voltage to electrodes forming an anode and a cathode, said electrolyzing device receiving a mixture of the raw water and chloride solution from the mixer and producing an acidic liquid on an anode side and an alkaline liquid on a cathode side by electrolyzing the mixture;

a measuring device for measuring a concentration of hypochlorous acid contained in the acidic liquid produced on the anode side; and a control device means connected to the measuring device and the electrodes, said control device means adapted to periodically switching polarities of the electrodes for protecting the electrodes and controlling an electrolytic condition in the electrolyzing device with an inverse sawteeth pattern adapted for switching of the polarities so that a measured concentration of the hypochlorous acid formed at the anode side is substantially constant, said inverse sawteeth pattern including a gradual increase from a predetermined low value to a predetermined high value and a rapid decrease from the high value to the low value between a condition right after changing the polarity and a condition after a next change of the polarity.

2. An electrolytic water producing apparatus according to claim 1, wherein in case the polarities of the electrodes are changed without controlling the electrolytic condition, the measuring device is adapted to provide a repetition of a change of the measured concentration of hypochlorous acid between a rapid increase from a low value to a high value and a gradual decrease from the high value to the low value as a passage of time, said rapid increase occurring when the polarities are switched.

3. An electrolytic water producing apparatus according to claim 1, wherein said control device means is adapted to control at least one of an electrolytic voltage applied to the electrodes, an electrolytic current applied to the electrodes, a supply quantity of the chloride solution to the electrolyzing device, and supply quantity of the raw water to the electrolyzing device.

4. An electrolytic water producing apparatus according to claim 3, wherein in case one of the electrolytic voltage and the electrolytic current applied to the electrodes is changed, one of the voltage and the current is reduced by the control device means when the concentration of hypochlorous acid is high, and is gradually increased as the concentration of hypochlorous acid is reduced.

5. An electrolytic water producing apparatus according to claim 3, wherein in case the supply quantity of the chloride solution is changed, the supply quantity of the chloride solution is reduced by the control device means when the concentration of hypochlorous acid is high, and is gradually increased as the concentration of hypochlorous acid is reduced.

6. An electrolytic water producing apparatus according to claim 3, wherein in case the supply quantity of the raw water is changed, the supply quantity of the raw water is increased by the control device means when the concentration of hypochlorous acid is high, and is gradually reduced as the concentration of hypochlorous acid is reduced.

7. An electrolytic water producing apparatus according to claim 4, wherein said one of the electrolytic voltage and the electrolytic current applied to the electrodes is determined as a predetermined pattern in advance for controlling the concentration of hypochlorous acid, said predetermined pattern being memorized in the control device.

8. An electrolytic water producing apparatus according to claim 7, wherein when the concentration of hypochlorous acid is changed as a whole upon measurement thereof by the measuring device and wherein, said predetermined pattern is changed as a whole according to the change of the concentration.

* * * * *